(12) United States Patent
Gallen et al.

(10) Patent No.: US 9,393,151 B2
(45) Date of Patent: Jul. 19, 2016

(54) APPARATUS AND METHOD FOR THERMAL THERAPY TREATMENT TO MALE GENITALIA

(75) Inventors: Mila Michael Gallen, West Orange, NJ (US); Gordon Randall Perry, New York, NY (US)

(73) Assignee: Mila Michael Gallen, Irvine, CA (US)

( * ) Notice: Subject to any disclaimer, the term of this patent is extended or adjusted under 35 U.S.C. 154(b) by 788 days.

(21) Appl. No.: 13/523,288

(22) Filed: Jun. 14, 2012

(65) Prior Publication Data

US 2013/0338742 A1   Dec. 19, 2013

(51) Int. Cl.
| A61F 7/02 | (2006.01) |
|---|---|
| A61F 7/10 | (2006.01) |
| A61F 7/03 | (2006.01) |
| A61F 7/00 | (2006.01) |

(52) U.S. Cl.
CPC ... *A61F 7/02* (2013.01); *A61F 7/03* (2013.01); *A61F 7/10* (2013.01); *A61F 7/106* (2013.01); *A61F 2007/0048* (2013.01); *A61F 2007/0228* (2013.01); *A61F 2007/0231* (2013.01); *A61F 2007/0242* (2013.01); *A61F 2007/108* (2013.01)

(58) Field of Classification Search
CPC .................. A61F 2007/0048; A63B 71/1216; A41B 9/023
USPC ............ 607/108, 112, 113; 2/403; 602/70–73
See application file for complete search history.

(56) References Cited

U.S. PATENT DOCUMENTS

| 1,477,187 | A | * | 12/1923 | Rayne ............................. 602/71 |
|---|---|---|---|---|
| 4,073,289 | A | | 2/1978 | Fahim |
| 4,378,010 | A | | 3/1983 | McDonald |
| 4,413,624 | A | | 11/1983 | Snow |
| 4,471,772 | A | | 9/1984 | Miller, Jr. |
| 4,590,931 | A | | 5/1986 | Kidwell, Jr. |
| 5,063,939 | A | | 11/1991 | Walston |
| 5,094,234 | A | | 3/1992 | Searcy |
| 5,226,179 | A | | 7/1993 | Choi |
| 5,243,974 | A | | 9/1993 | Allen |
| 5,514,170 | A | | 5/1996 | Mauch |
| 5,716,319 | A | | 2/1998 | Sembert |
| 5,766,235 | A | | 6/1998 | Kostopoulos |
| 5,887,437 | A | | 3/1999 | Maxim |
| 5,897,581 | A | * | 4/1999 | Fronda et al. ................. 607/109 |
| 5,935,595 | A | * | 8/1999 | Steen ............................. 424/443 |
| 6,068,607 | A | * | 5/2000 | Palmer et al. .................... 602/67 |
| 6,308,341 | B1 | | 10/2001 | Shelton |
| 6,602,213 | B1 | | 8/2003 | Figley |
| 6,712,841 | B2 | | 3/2004 | Gomez |
| 7,744,640 | B1 | * | 6/2010 | Faries et al. .................... 607/109 |
| 7,788,739 | B1 | | 9/2010 | Della Ratta |
| 8,535,364 | B2 | * | 9/2013 | Margolis ................... A61F 7/10 2/400 |
| 2005/0085752 | A1 | | 4/2005 | Sells, II |
| 2006/0211974 | A1 | | 9/2006 | Bland |

(Continued)

*Primary Examiner* — Joseph Stoklosa
*Assistant Examiner* — Adam Avigan
(74) *Attorney, Agent, or Firm* — Kirschstein, Israel, Schiffmiller & Pieroni, P.C.

(57) ABSTRACT

An apparatus for thermal therapy treatment of male genitalia includes a contoured cup for receiving the male genitalia in a close, confronting, confining relationship therein, and an adjustable body harness connected to the cup for holding and maintaining the cup in a treatment position in which pressure is exerted against the genitalia. The cup has a contoured inner shell for receiving the genitalia, a contoured outer shell permanently and irremovably sealed to the inner shell, and a thermal medium permanently sealed in an internal chamber between the shells.

18 Claims, 4 Drawing Sheets

(56) References Cited

U.S. PATENT DOCUMENTS

| | | |
|---|---|---|
| 2008/0010716 A1 | 1/2008 | Brown |
| 2008/0027383 A1 | 1/2008 | Nahhas |
| 2009/0105793 A1* | 4/2009 | Brown et al. .................. 607/108 |
| 2009/0171260 A1* | 7/2009 | Lerma ............................. 602/72 |
| 2010/0094386 A1 | 4/2010 | Margolis |
| 2011/0009794 A1* | 1/2011 | Diamond et al. ............... 602/70 |

* cited by examiner

US 9,393,151 B2

APPARATUS AND METHOD FOR THERMAL THERAPY TREATMENT TO MALE GENITALIA

FIELD OF THE DISCLOSURE

The present disclosure relates generally to an apparatus for, and a method of, thermal therapy treatment to male genitalia and, more particularly, to applying a cooling/heating treatment temperature and/or a treatment pressure directly to targeted portions of a scrotal area, especially for, but not limited to, mitigating post-operative or post-trauma complications, such as swelling, bruising, inflammation, hemorrhaging, pain, and like symptoms, of a scrotum and/or a penis.

BACKGROUND

It is generally known to apply cold compresses to male genitalia to relieve swelling, bruising, inflammation, hemorrhaging, pain and like symptoms/complications caused by a trauma, e.g., a sports injury, or by a surgical procedure, e.g., a vasectomy, a circumcision, or a urological disease associated with the treatment of epididymitis, orchitis, hydroceles, spermatoceles, varicoceles, inguinal hernia repair, cancer, gonorrhea, clamydia, etc. Cold compresses have also been applied to male genitalia to promote male fertility. It is also known to apply heating packs/pads to male genitalia for post-operative treatment to manage pain, to dilate blood vessels in targeted tissue, and to enhance perfusion to the targeted tissue.

Yet, despite their beneficial therapeutic effects, it is often difficult to apply the cold compresses/heating packs to swollen/affected scrotal areas of differently sized individuals suffering from different levels of injury due to the different anatomical locations, shapes, and sizes of the swollen/affected scrotal areas. Sometimes, the individuals are generally supine and may even be anesthetized or unconscious. Often, ice, water bags, or frozen gel packs are simply placed on top of an individual's penis, thereby only partially cooling the individual's scrotum, and applying very little, if any, pressure directly to the swollen/affected scrotal areas. Sometimes, rolled-up towels are placed underneath the scrotum to increase blood circulation. However, such towels often shift relative to the individual over time, thereby decreasing their efficacy.

Sometimes, frozen gel packs are removably placed in pockets within a cloth garment to be worn over an individual's pelvic area. Yet, such gel pack-filled pockets may not directly overlie, or provide any significant pressure directly to, the swollen/affected scrotal area, thereby leading to an ineffective cooling pressure treatment. In any event, it is often difficult for heath care workers to position and arrange such a cloth garment on a lower torso of a supine/anesthetized/unconscious individual.

Accordingly, there is a need for an apparatus and method for treating male genitalia, both human and animal, with thermal therapy by effectively applying a cooling/heating temperature and/or a treatment pressure directly to targeted portions of a scrotal area for various purposes, such as the relief and treatment of post-operative and post-trauma symptoms/complications, as well as for the enhancement of male fertility.

BRIEF DESCRIPTION OF THE FIGURES

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
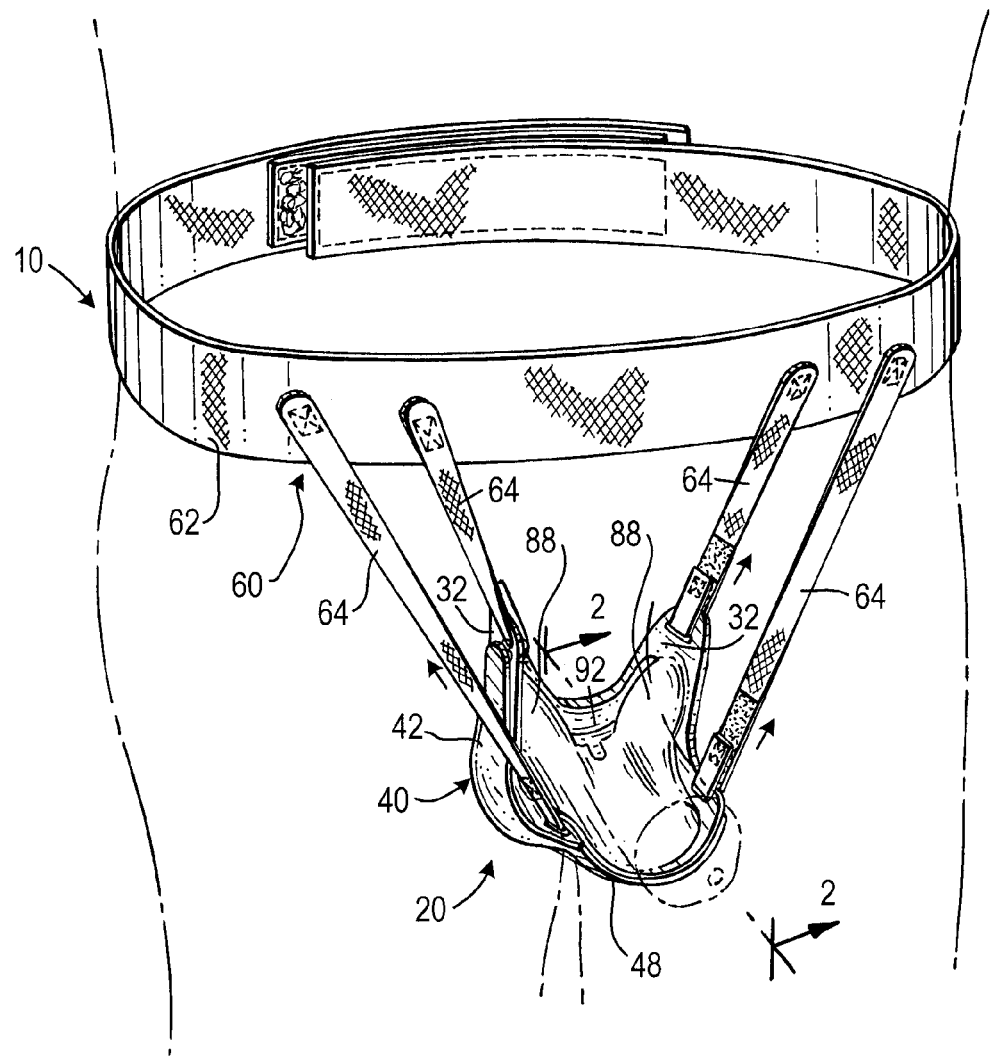
FIG. 1 is a perspective view of an apparatus for treating male genitalia with thermal therapy prior to adjustment to a treatment position in accordance with this invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

In accordance with one feature of this invention, an apparatus for thermal therapy treatment of male genitalia, both human and animal, includes a contoured cup for receiving the male genitalia in a close, confronting, confining relationship during treatment. The cup has a contoured inner shell bounding a compartment for receiving a scrotum of the male genitalia during treatment; a contoured outer shell juxtaposed and nested with, and permanently and irremovably sealed to, the inner shell to bound an internal chamber with the inner shell; and a thermal medium, typically a cooling/heating fluid, permanently sealed in the internal chamber between the shells. The outer shell has shape-retaining support walls for supporting and holding the inner shell in at least partly surrounding relationship with, and for supporting and holding the thermal medium in thermal communication with, the scrotum in the compartment during the treatment. A body harness is connected to the cup for maintaining the cup in a treatment position in which the scrotum is received inside the compartment during the treatment.

Advantageously, the outer shell is constituted of a shape-retaining material that maintains, or returns to, its shape in the treatment position. Such a material is preferably semi-rigid and not readily flexible, such as a resilient plastic, but may also be hard, stiff and rigid. The outer shell material is also thermally insulating so as to resist thermal loss of the thermal medium through the outer shell. The support walls of the outer shell have a pair of generally upright, side walls at opposite sides of the scrotum, and a base wall at a bottom of the scrotum and extending between the support walls. The outer shell further has a shape-retaining extension wall extending in a longitudinal direction away from the support walls to support and hold the inner shell in engagement with, and to support and hold the thermal medium in thermal communication with, a penis of the male genitalia during treatment. All of the walls of the outer shell are preferably integral with one another in a one-piece molded plastic construction.

Advantageously, the inner shell is constituted of a sheet, preferably, a thin, flexible plastic film or membrane capable of readily conforming to the contour of the outer shell and capable of conducting heat or cold therethrough. The sheet conformably overlies the outer shell, and is permanently sealed to the outer shell along a circumferentially-complete outer seal surrounding the internal chamber to maintain the thermal medium therein without leakage. The sheet has side portions overlying a pair of sub-chambers filled with the thermal medium. The side portions are located at, and contact, the opposite sides of the scrotum in the treatment position. The sheet also has a ridge overlying a ridge chamber filled with the thermal medium. The ridge contacts and lifts a bottom of the scrotum in the treatment position. In an alternative embodiment, the side portions and the ridge may be shaped by providing various inner seals within the internal chamber. One of the inner seals is a subdividing seal that subdivides the internal chamber into the pair of sub-chambers filled with the thermal medium. Another of the inner seals is a ridge seal that forms the ridge chamber filled with the thermal medium. Preferably, each outer seal and inner seal is a heat-fused seal or weld, but an adhesive could also be used. The inner seals are optional.

Advantageously, the sheet has an extension portion juxtaposed with, and permanently and irremovably sealed to, the extension wall to bound an extension sub-chamber of the internal chamber that is filled with the thermal medium. The extension wall supports and holds the extension portion in engagement with, and supports and holds the thermal medium in the extension sub-chamber in thermal communication with, a penis of the male genitalia in the treatment position.

In one embodiment, the thermal medium is a cooling medium and is advantageously re-usable and re-coolable to a cold treatment temperature, in which case, the thermal medium can be water or a gel, as described in detail below. In another embodiment, the cooling medium is advantageously coolable only once to the cold treatment temperature, as also described in detail below. In still another embodiment, the thermal medium is a heating medium and is advantageously re-usable and re-heatable to a hot treatment temperature, in which case, the thermal medium can be water or a chemical solution, as described in detail below. In yet another embodiment, the heating medium is advantageously heatable only once to the hot treatment temperature, as also described in detail below.

The body harness insures that the thermal treatment temperature is directly applied, together with the exertion of pressure, against targeted portions of the male genitalia. Advantageously, the body harness includes a waist belt and a plurality of, e.g., four, elongated straps extending longitudinally from the belt to the cup. At least one of the straps, and preferably, each strap, is adjustable lengthwise to position the cup in the treatment position and to apply pressure against the male genitalia.

Figure 3:
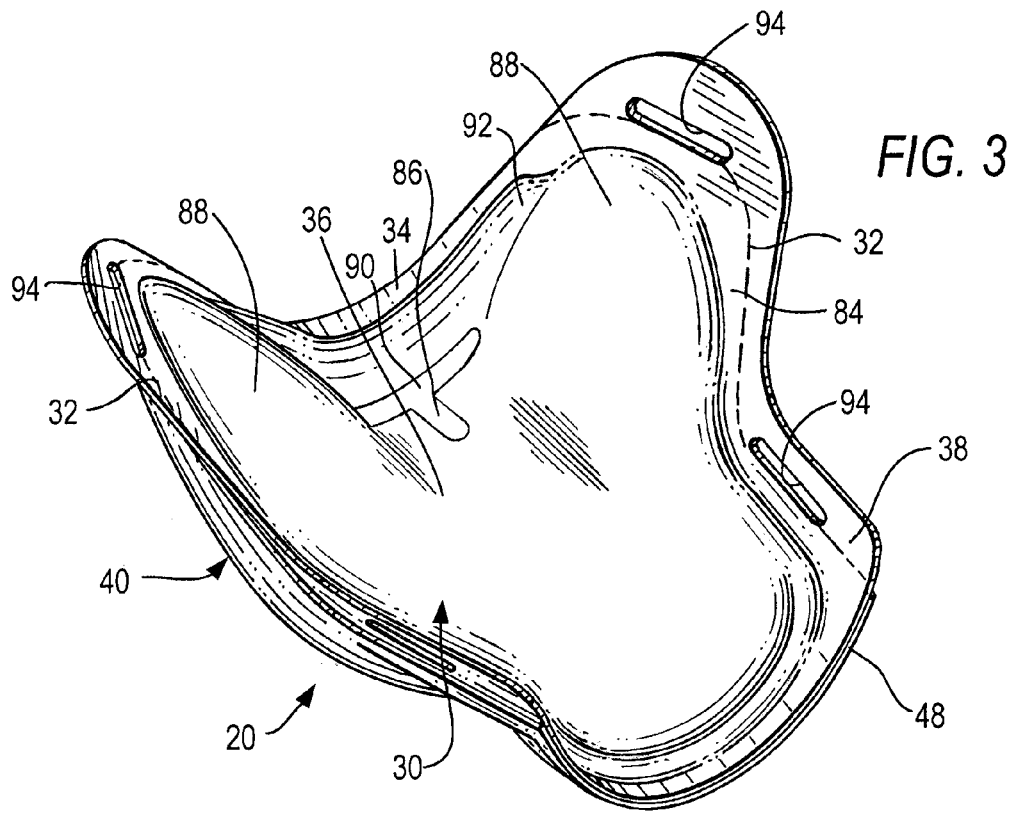
FIG. 3 is a perspective view of a cup of the apparatus of FIG. 1.
Figure 4:
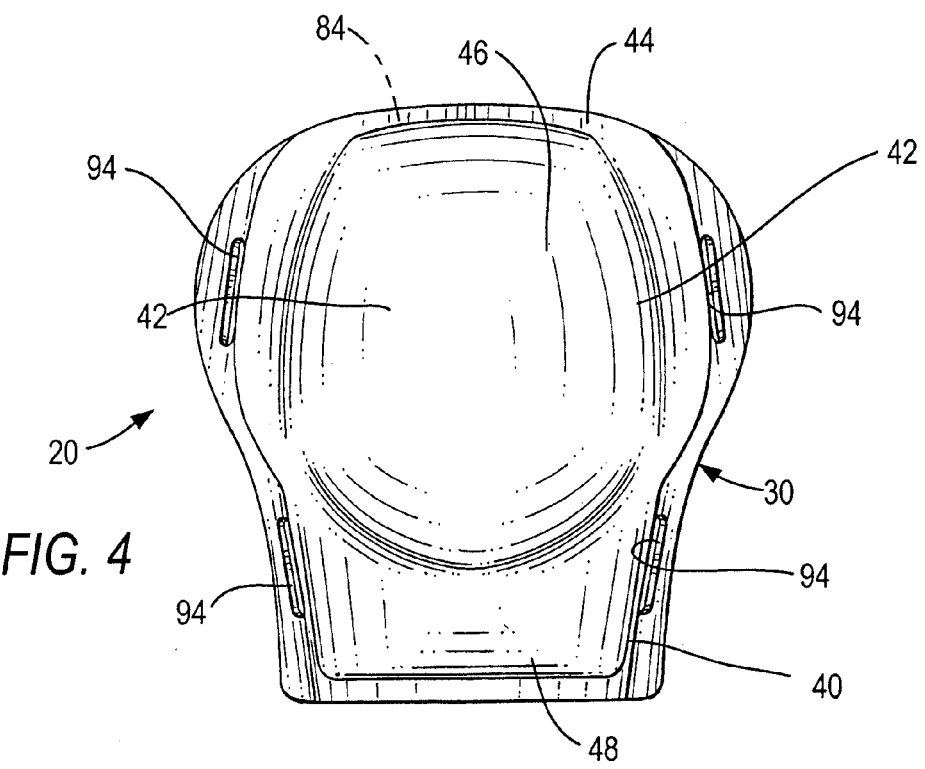
FIG. 4 is a bottom plan view of the cup of FIG. 3.
Figure 5:
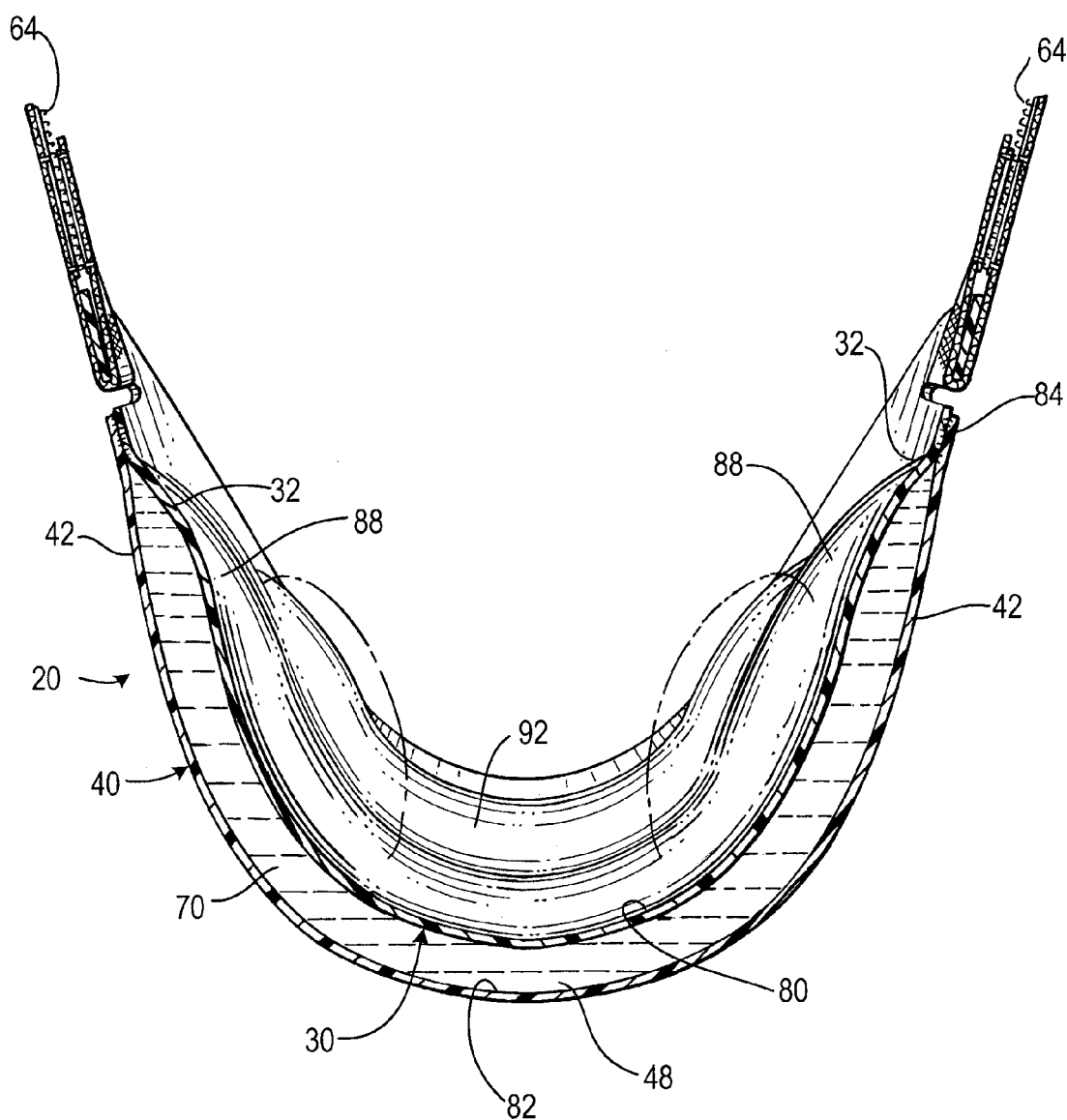
FIG. 5 is a sectional view taken on line 5-5 of FIG. 2.

Turning now to the drawings, reference numeral 10 in FIG. 1 generally identifies an apparatus for thermal (cold or hot) therapy treatment of male genitalia (shown in broken lines throughout the figures), and includes a contoured cup 20 and a body harness 60 for holding and maintaining the cup 20 in a treatment position in which the male genitalia are received in a close, confronting, confining relationship in the cup 20, as best illustrated and described below in connection with FIG. 2. The cup 20, shown in isolation in FIGS. 3-4, has a contoured inner shell 30 or liner bounding a compartment 80 for receiving a scrotum of the male genitalia during treatment; a contoured outer shell 40 or jacket juxtaposed with, and permanently and irremovably sealed to, the inner shell 30 to bound an internal chamber 82 with the inner shell 30; and a thermal medium 70, typically a fluid, permanently sealed in the internal chamber 82 between the shells 30, 40.

The outer shell 40 is constituted of a shape-retaining material that maintains, or returns to, its shape in the treatment position. Such a material is preferably semi-rigid and not readily flexible, such as a resilient plastic, but may also be hard, stiff and rigid. The material of the outer shell 40 is also thermally insulating so as to resist thermal loss of the thermal medium through the outer shell. Many types of thermally insulating plastic materials, e.g., polyamides, are suitable for this purpose. The outer shell 40 has shape-retaining support walls for supporting and holding the inner shell 30 in at least partly surrounding engagement with, and for supporting and holding the thermal medium 70 in thermal communication with, the scrotum in the compartment during the treatment. The support walls includes a pair of generally upright, outer side walls 42, 42 spaced and maintained apart of one another at opposite sides of the scrotum, a outer base wall 44 extending between the side walls 42, 42, and an outer bottom wall 46 also extending between the side walls 42, 42. The outer shell 40 also has a shape-retaining extension wall 48 extending in a longitudinal direction away from the side walls 42, 42. All of the walls 42, 44, 46, 48 of the outer shell 40 are preferably integral with one another in a one-piece molded plastic construction. The walls 42, 44, 46 are curved so that the compartment 80 is generally hemispherical in shape. The extension wall 48 is also curved and has a generally U-shaped cross-section.

The inner shell 30 is constituted of a sheet, preferably, a thin, flexible plastic film or membrane capable of readily conforming to the contour of the outer shell 40 and capable of conducting heat or cold therethrough. The inner shell 30 conformably overlies the outer shell 40, and is permanently sealed to the outer shell 40 along a circumferentially-complete outer seal 84 surrounding the internal chamber 82 to maintain the thermal medium 70 therein without fluid leakage. The inner shell 30 has a pair of generally upright, inner side walls 32, 32 overlying the outer side walls 42, 42, an inner base wall 34 overlying the outer base wall 44, an inner bottom wall 36 overlying the outer bottom wall 46, and an extension portion 38 overlying the extension wall 48. All of the walls 32, 34, 36, 38 of the inner shell 30 are integral with one another in a one-piece molded plastic sheet and, due to their thinness and flexibility, generally conform to the generally hemispherical shape of the outer shell 40 and the generally U-shaped extension wall 48.

The inner shell 30 has a pair of side portions 88, 88 overlying a pair of sub-chambers filled with the thermal medium 70. The side portions 88, 88 are located at, and contact, the opposite sides of the scrotum in the treatment position. The inner shell 30 also has a ridge 92 overlying a ridge chamber filled with the thermal medium. The ridge 92 contacts and lifts a bottom of the scrotum in the treatment position.

In an alternative embodiment, the side portions 88, 88 and the ridge 92 may be shaped by providing various inner seals within the internal chamber 82. One of the inner seals is a subdividing seal 86 that subdivides the internal chamber 82 into the pair of sub-chambers filled with the thermal medium 70. Another of the inner seals is a ridge seal 90 that forms the ridge chamber filled with the thermal medium. Preferably, each outer seal and inner seal is a heat-fused seal or weld, but an adhesive could also be used. The inner seals 86, 90 are optional.

In one embodiment, the thermal medium 70 is a cooling medium and is advantageously re-usable and re-coolable to a cold treatment temperature, in which case, the thermal medium can be water or a gel. Preferably, the gel comprises one or more water-swellable polymeric components. Such water-swellable polymeric components are well known and are often referred to as hydrophilic polymeric components or materials, or hydrogel-forming polymeric components or materials. One very useful water-swellable polymeric component includes one or more polyacrylic acid components and the like. However, it should be noted that other formulations, and one or more other suitable water-swellable polymeric components may be used or included in the gel, and such other formulations and other water-swellable polymeric component or components are included within the scope of the present invention. The gel may have a water content sufficient to swell the gel, for example, in a range of about 40% or about 60% or about 75% to about 95% by weight of the gel. The gel advantageously is cooled to a cold treatment temperature of about 35 degrees Fahrenheit. The gel advantageously is malleable at the cold treatment temperature, but the gel can also be formulated to be less malleable, if not frozen solid, at the cold treatment temperature. Water can be cooled to, or above, or below, its freezing point.

In another embodiment, the cooling medium 70 is advantageously coolable only once to the cold treatment temperature. In this one-time, disposable usage, the thermal medium typically contains a chemical pack, e.g., ammonium nitrate, and a water pack separated from the chemical pack by a breakable membrane. When the membrane is broken and breached, the contents of the chemical and the water packs mix together, and an endothermic reaction involving the absorption of heat is generated. The ammonium nitrate mixing with the water creates cold, and a cold treatment temperature, for example, on the order of 32 degrees Fahrenheit can be reached. This cold treatment temperature can normally be maintained for approximately thirty minutes, if not longer, depending on the formulation of the chemical pack.

In still another embodiment, the thermal medium 70 is a heating medium and is advantageously re-usable and re-heatable to a hot treatment temperature, for example, on the order of 140 degrees Fahrenheit, in which case, the thermal medium can be water, or a chemical solution, such as a supersaturated solution of sodium acetate in water. A small flat disc of notched ferrous metal in the solution is flexed to release crystals of sodium acetate into the solution, which then act as nucleation sites for the crystallization of the sodium acetate into a hydrated salt, i.e., sodium acetate trihydrate. Because the solution is supersaturated, the solution crystallizes suddenly, thereby releasing heat. The heating medium can be re-used by placing it in boiling water for several minutes, or in a microwave oven, which re-dissolves the sodium acetate trihydrate in the water and recreates the supersaturated solution. Once the heating medium has returned to room temperature, it can be triggered again.

In yet another embodiment, the heating medium 70 is advantageously heatable only once to the hot treatment temperature. In this one-time, disposable usage, the heating medium employs a one-time, exothermic chemical reaction, such as catalyzed rusting of iron, or dissolving of calcium chloride. The reagents are kept in separate compartments by a breakable membrane. When the membrane is broken, the reagents mix together, thereby producing heat.

The body harness 60 insures that the thermal treatment temperature is directly applied, together with the exertion of a treatment pressure, against targeted portions of the male genitalia. Advantageously, the body harness 60 includes a waist belt 62 and a plurality of, e.g., four, longitudinal straps 64 extending from the belt 62 to the cup 20. The belt 62 is adjustable, e.g., by a hook-and-loop fastener or the like, to fit securely around a waist of an individual. At least one of the straps, and preferably, each strap 64, is adjustable lengthwise to position the cup 20 in the treatment position of FIG. 2 and to apply targeted pressure against the male genitalia. One end of each strap 64 is connected, e.g., by being sewn, to a front of the belt 62. The opposite end of each strap 64 bears a hook-and-loop fastener or the like, and is looped through a respective one of a corresponding plurality of mounting slots 94 provided on the cup 20. Thus, each strap 64 is pulled as taut as desired prior to securing the respective strap with its hook-and-loop fastener. By being accessible at the front of the belt 62, the straps are easily adjustable, even by health care workers who are tending to a supine, anesthetized or unconscious individual.

Figure 2:
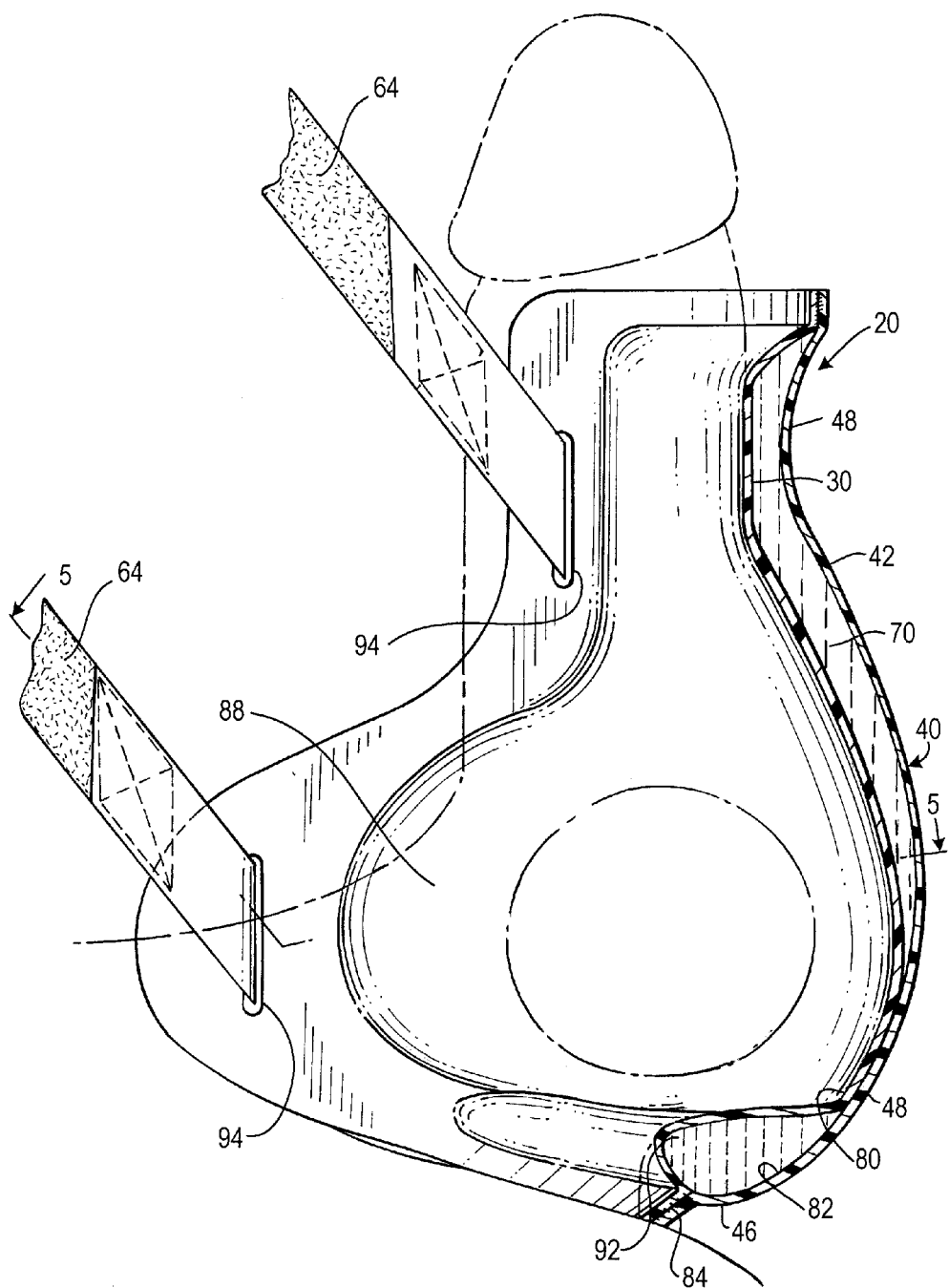
FIG. 2 is an enlarged, broken-away, sectional view taken on line 2-2 of FIG. 1 after adjustment to the treatment position, with the male genitalia shown in broken lines.

FIG. 2 depicts the aforementioned, preferred treatment position in which the straps 64 are adjusted such that a scrotum of the male genitalia is received in the compartment 80, and a penis of the male genitalia is supported in a generally upright vertical condition. The outer side walls 42, 42 support and hold the side portions 88, 88 in engagement with, and support and hold the thermal medium 70 in the sub-chambers in thermal communication with, opposite sides of the scrotum in the compartment 80. The base wall 44 supports and holds the ridge 92 in engagement with, and supports and holds the thermal medium 70 in the ridge chamber in thermal communication with, the bottom of the scrotum in the compartment 80. The ridge 92 also lifts the bottom of the scrotum and the testicles therein to increase blood circulation in this scrotal region. The ridge 92 contacts the scrotum along an elongated band or zone behind the testicles, thereby targeting its thermal effect. The extension wall 48 that overlies the extension portion 38 forms an extension sub-chamber therewith. The extension wall 48 supports and holds the extension portion 38 in engagement with, and supports and holds the thermal medium in the extension sub-chamber in thermal communication with, the penis in the treatment position.

The cooling medium is either cooled or frozen by being placed in a refrigerator or freezer in advance of the thermal therapy treatment, or is activated in situ according to the one-time, disposable usage described above. The heating medium is heated by being placed in boiling water or a microwave oven in advance of the thermal therapy treatment, or is activated in situ according to the one-time, disposable usage described above.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having,"

"includes," "including," "contains," "containing," or any other variation thereof, are intended to cover a non-exclusive inclusion, such that a process, method, article, or apparatus that comprises, has, includes, or contains a list of elements does not include only those elements, but may include other elements not expressly listed or inherent to such process, method, article, or apparatus. An element proceeded by "comprises . . . a," "has . . . a," "includes . . . a," or "contains . . . a," does not, without more constraints, preclude the existence of additional identical elements in the process, method, article, or apparatus that comprises, has, includes, or contains the element. The terms "a" and "an" are defined as one or more unless explicitly stated otherwise herein. The terms "substantially," "essentially," "approximately," "about," or any other version thereof, are defined as being close to as understood by one of ordinary skill in the art, and in one non-limiting embodiment the term is defined to be within 10%, in another embodiment within 5%, in another embodiment within 1%, and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

We claim:

1. An apparatus for thermal therapy treatment of male genitalia, comprising:
    a contoured cup configured to receive the male genitalia and having
    an outer shell constituted of a rigid or semi-rigid shape-retaining material,
    an inner shell constituted of a flexible material and juxtaposed with the outer shell,
    a circumferentially-complete outer seal for permanently sealing the shells together to bound a permanently sealed internal chamber between the shells, and
    a thermal treatment fluid permanently sealed in the internal chamber and maintained between the shells by the outer seal without fluid leakage; and
    a body harness connected to the cup and configured for holding the male genitalia received in the cup in a treatment position, the body harness including a waist belt having a front portion adapted to be positioned anterior to a wearer and a rear portion adapted to be positioned posterior to the wearer, and a plurality of longitudinal front straps each front strap extending from the front portion of the belt directly to the cup, each front strap extending along its entire length only between the front portion of the belt and the cup in the treatment position and not extending to the rear portion of the belt to provide front access to the font straps, at least one of the front straps adapted to be adjustable and, pulled taut to position the cup in the treatment position and to apply a treatment pressure directly against targeted portions of the male genitalia during treatment.

2. The apparatus of claim 1, wherein the material of the outer shell is a thermally insulating material, and wherein the material of the inner shell is a thermally conducting material.

3. The apparatus of claim 1, wherein the outer shell has a pair of generally upright, outer side walls and an outer base wall, and wherein the outer base wall extends between, and is integral in a one-piece construction with, the outer side walls.

4. The apparatus of claim 3, wherein the inner shell has a pair of generally upright, inner side walls that overlie, and are spaced by the treatment fluid from, the outer side walls of the outer shell; and an inner base wall that overlies, and is spaced by the treatment fluid from, the outer base wall of the outer shell; and wherein the inner base wall extends between, and is integral in a one-piece construction with, the inner side walls.

5. The apparatus of claim 4, wherein the outer shell has an outer extension wall extending in a longitudinal direction away from, and integral in a one-piece construction with, the outer side walls; and wherein the inner shell has an inner extension wall extending in the longitudinal direction away from, and integral in a one-piece construction with, the inner side walls; and wherein the outer and inner extension walls overlie each other and bound an extension sub-chamber of the internal chamber that is filled with the thermal fluid.

6. The apparatus of claim 1, wherein the inner shell has a pair of side portions that are configured to directly contact opposite sides of a scrotum of the male genitalia in the treatment position, and wherein the side portions overlie a pair of sub-chambers of the internal chamber filled with the thermal fluid.

7. The apparatus of claim 6, wherein the shells are sealed along an inner subdividing seal for subdividing the internal chamber into the pair of sub-chambers.

8. The apparatus of claim 1, wherein the inner shell has a ridge portion that is configured to directly contact and lift a bottom of a scrotum of the male genitalia in the treatment position, and wherein the ridge portion overlies a ridge chamber of the internal chamber filled with the thermal fluid.

9. The apparatus of claim 8, wherein the shells are sealed along an inner ridge seal for forming the internal chamber with the ridge chamber.

10. The apparatus of claim 1, wherein the thermal fluid is a cooling fluid re-usable and re-coolable to a cold temperature sufficient to effect the thermal therapy treatment.

11. The apparatus of claim 1, wherein the thermal fluid is a heating fluid re-usable and re-heatable to a hot temperature sufficient to effect the thermal therapy treatment.

12. The apparatus of claim 1, wherein the thermal fluid is settable only once to a temperature sufficient to effect the thermal therapy treatment.

13. The apparatus of claim 1, wherein the cup has a plurality of mounting slots, and wherein each strap is looped through a respective slot.

14. The apparatus of claim 1, wherein the cup has a plurality of mounting slots, and wherein each front strap has one end connected to the front portion of the belt, and an opposite end looped through a respective slot and fastened onto the respective front strap.

15. The apparatus of claim 14, wherein the opposite end of each front strap has a hook-and-loop fastener.

16. The apparatus of claim 14, wherein the cup has four corner regions, and wherein there are four of the mounting slots respectively located at the four corner regions of the cup, and wherein there are four of the front straps that are respectively looped through the respective mounting slots to support the cup in the treatment position.

17. A method of treating male genitalia with thermal therapy, comprising:

receiving the male genitalia in a contoured cup formed by juxtaposing a rigid or semi-rigid outer shell and a flexible inner shell, by permanently sealing the shells together with a circumferentially complete outer seal to bound a permanently sealed internal chamber between the shells, and by permanently sealing and maintaining a thermal treatment fluid in the internal chamber between the shells without fluid leakage;

holding the male genitalia received in the cup in a treatment position by connecting a body harness to the cup;

configuring the body harness with a waist belt having a front portion anterior to a wearer, a rear portion posterior to the wearer, and with a plurality of adjustable front straps, and by connecting each front strap from the front portion of the belt directly to the cup;

providing front access to the front straps by extending each front strap along its entire length only between the front portion of the belt and the cup during treatment, and by not extending each front strap to the rear portion of the belt; and applying a treatment pressure directly against targeted portions of the male genitalia during treatment by adjusting the body harness by pulling at least one of the front straps taut to position the cup over the male genitalia during treatment and to apply the treatment pressure directly against the target portion of the male genitalia.

18. The method of claim 17, and configuring the cup with a plurality of mounting slots, and by looping each strap through a respective slot.

* * * * *